US00PP28486P2

(12) United States Plant Patent
Sato et al.

(10) Patent No.: US PP28,486 P2
(45) Date of Patent: Oct. 3, 2017

(54) **NEW GUINEA *IMPATIENS* PLANT NAMED 'SAKIMP043'**

(50) Latin Name: ***Impatiens hybrida* hort**
Varietal Denomination: SAKIMP043

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,132

(22) Filed: Mar. 31, 2016

(51) Int. Cl.
*A01H 5/02* (2006.01)

(52) U.S. Cl.
USPC ..... Plt./318.4

(58) Field of Classification Search
USPC ..... Plt./318.4, 318.1
CPC ..... A01H 5/0261
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

An *Impatiens* plant particularly distinguished by having blush-pink flowers with darker splotches at the base of the petal, and green leaves, is disclosed.

2 Drawing Sheets

Genus and species: *Impatiens hybrida* hort.
Variety denomination: 'SAKIMP043'.

BACKGROUND OF THE NEW PLANT

The present invention comprises a new and distinct variety of New Guinea *impatiens* plant, botanically known as *Impatiens hybrida* hort, and referred to by the variety name 'SAKIMP043'. 'SAKIMP043' originated in Misato, Japan from an interspecific hybridization between the proprietary female *Impatiens* variety 'NC-1H1' (unpatented) having light-orange flowers and the proprietary male *Impatiens* variety 'NJ-1174A' (unpatented) having lavender-colored flowers.

In January 2010, 'NC-1H1' and 'NJ-1174A' were crossed and a population of F1 plants was created. The F1 plants were evaluated in Misato, Japan in an open-field trial. The criteria for plant selection included light flower color, canopy-shaped plant habit, and a strong root system. At the completion of the trial, a single plant selection was made and given the experimental name 'M2013-444' based on the criteria above and vegetatively propagated. From June to August 2013, 'M2013-444' was evaluated in an open-field in Misato, Japan. Shoot-tip cuttings of the variety were then shipped to Salinas, Calif. where the plants were propagated and re-evaluated for stability of traits. 'M2013-444' was subsequently named 'SAKIMP043'. 'SAKIMP043' was found to reproduce true to type in successive generations of asexual propagation via vegetative cuttings in Salinas, Calif.

SUMMARY

The following are the most outstanding and distinguishing characteristics of this new variety when grown under normal horticultural practices in Salinas, Calif.

1. Blush-pink flowers with darker splotches at the base of the petal; and
2. Green leaves.

DESCRIPTION OF THE PHOTOGRAPHS

This *Impatiens* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
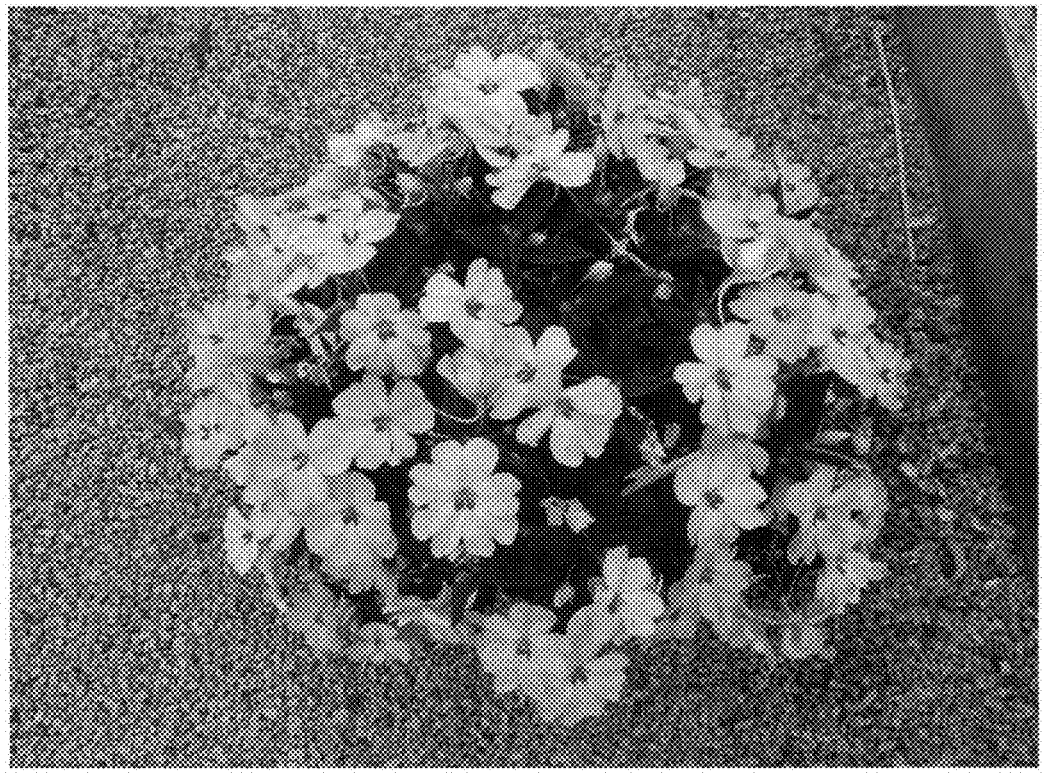
FIG. 1 shows the overall plant habit of the plant grown in a pot.
Figure 2:
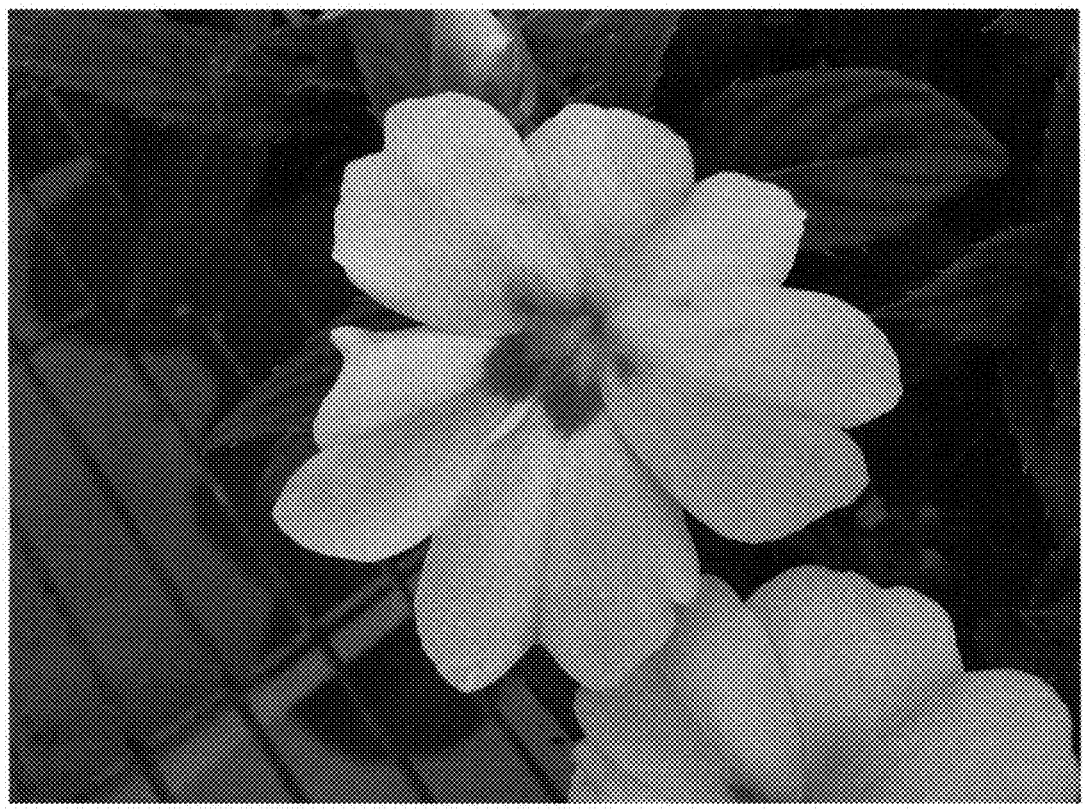
FIG. 2 shows a close-up of the mature inflorescence of the plant.

The following detailed descriptions set forth the distinctive characteristics of 'SAKIMP043'. Color references are to The Royal Horticultural Society of London color chart (R.H.S.), $4^{th}$ edition (2001). Anatomic labels are from *The Cambridge Illustrated Glossary of Botanical Terms*, by M. Hickey and C. King, Cambridge University Press.

Classification:

*Family*.—Balsaminaceae.
*Botanical*.—*Impatiens hybrida* hort.
*Common*.—*Impatiens*.
*Designation*.—'SAKIMP043'.

Growth:

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2 to 3 days, 2 times in consecutive applications and then given one clear water application. Pots were top-dressed with a dry, slow release fertilizer containing 20% nitrogen, 10% phosphorus and 18% potassium. The typical average air temperature was 24° C.

Parentage:

*Female parent*.—The proprietary female *Impatiens* variety 'NC-1H1' (unpatented).

*Male parent*.—The proprietary male *Impatiens* variety 'NJ-1174A' (unpatented).

Plant description:

*Life cycle*.—Annual.

*Habit*.—Spreading, dense.

*Height*.—17.5 cm from soil line to the top of the foliage.

*Spread*.—38.0 cm.

*Number of branches per plant*.—8 main branches.

*Length of branches*.—Branching begins at soil line, 20.0 cm to 24.0 cm.

*Diameter of branches*.—1.3 cm for the main branch; 0.7 cm to 1.0 cm for the other secondary branches.

*Color of branches*.—Closest to RHS 60A (Red-purple) with slight RHS 144B (Yellow-green).

*Time to produce a rooted cutting*.—About 4 weeks.

*Time to bloom from propagation*.—6 to 8 weeks.

*Flowering requirements*.—Will flower so long as temperature is above 5° C.

*Temperature tolerances*.—Plants observed to continue flowering in a temperature range of 5° C. to 36° C.

Stems:

*Color*.—Closest to RHS 60A (Red-purple) with slight RHS 144B (Yellow-green).

*Anthocyanin color*.—RHS 60A (Red-purple).

*Pubescence*.—Absent.

*General description*.—Strong; circular in cross-section, smooth and shiny.

*Length*.—1.5 cm to 4.3 cm from the first node to the second node; 13.0 cm to 19.0 cm total.

*Diameter*.—5.0 mm to 7.0 mm.

*Internode length*.—3.7 cm to 4.5 cm.

Leaves:

*Arrangement*.—Whorled with up to 5 leaves per node, opposite if only two leaves at one node.

*Shape*.—Lanceolate, curled.

*Apex*.—Acuminate.

*Base*.—Shortly attenuate.

*Margin*.—Serrate.

*Surface appearance* (*both surfaces*).—Dull and waxy.

*Length*.—6.0 cm.

*Width*.—2.5 cm.

*Color*.—Upper surface: RHS 139A (Green). Lower surface: RHS 147B (Yellow-green).

*Variegation*.—Absent.

*Fragrance*.—Absent.

*Pubescence*.—Absent.

*Petiole*.—Length: 1.0 cm. Diameter: 3.0 mm. Color: Closest to RHS 145D (Yellow-green) with very slight RHS 60B (Red-purple) on most of the petiole. Texture: Smooth, glabrous.

*Venation*.—Pinnate.

*Venation color*.—Upper surface: RHS 145D (Yellow-green). Lower surface: Closest to RHS 138B (Green).

Flower buds:

*Surface texture*.—Glabrous.

*Length*.—1.5 cm.

*Diameter*.—1.0 cm.

*Shape*.—Deltoid, longitudinal in cross-section.

*Color*.—RHS 62A (Red-purple) with RHS 144A (Yellow-green) at the edge.

Flowers:

*Inflorescence type*.—Single flower with spur.

*Fragrance*.—Absent.

*Number of flowers per node*.—1 to 3 in bloom at one time; about 10 flower buds.

*Number of flowers per plant*.—Approximately 60 in bloom.

*Lastingness of individual flowers on the plant*.—14 days.

Corolla:

*Shape*.—Roughly circular with 5 radial petals.

*Diameter*.—5.3 cm.

*Depth*.—1.0 cm.

*Petals*.—Surface texture (both surfaces): Glabrous. Length: 3.1 cm. Width: 2.8 cm. Shape: Obcordate. Apex: Emarginate (cleaved). Base: Attenuate. Margin: Entire. Color: Upper surface: Closest to but lighter than RHS 52C (Red) for most petals, with other petals having a much lighter petal color closest to RHS 62D (Red-purple). Lower surface: Closest to RHS 56A (Red) for most petals, with other petals having a much lighter petal color closest to but lighter than RHS 56C (Red). Eye zone: Closest to RHS N34A (Orange-red).

Calyx:

*Sepal shape*.—Lanceolate.

*Sepal number per flower*.—2.

*Sepal length*.—1.0 cm.

*Sepal diameter*.—4.0 mm.

*Sepal apex*.—Caudate.

*Sepal base*.—Subcordate.

*Sepal margin*.—Entire.

*Sepal texture* (*both surfaces*).—Glabrous.

*Sepal color*.—Upper surface: Closest to RHS 145B (Yellow-green) with RHS 145D (Yellow-green) at the base and RHS 145A (Yellow-green) at the tip. Lower surface: Closest to RHS 145B (Yellow-green) with RHS 145D (Yellow-green) at the base and RHS 145A (Yellow-green) at the tip.

Spur:

*Color*.—RHS 155C (White) with slight RHS 144C (Yellow-green) at the tip.

*Shape*.—Tubular and curved downward.

*Length*.—5.5 cm.

*Diameter*.—1.0 mm to 2.0 mm.

Peduncle:

*Length*.—2.2 cm.

*Color*.—RHS 144C (Yellow-green) with very slight RHS 60A (Red-purple) at the base.

*Diameter*.—1.5 mm.

*Texture*.—Smooth and glabrous.

Reproductive organs:

*Stamens*.—Stamen form: Fused and split into 4 lobes. Stamen number per flower: 5. Filament form: Free. Anther length: 4.0 mm. Anther color: Closest to RHS 63B (Red-purple) but transparent. Pollen amount: Abundant. Pollen color: RHS 158B (Yellow-white). Pollen description: Powdery.

*Pistil*.—Pistil number per flower: 1. Stigma color: RHS 145D (Yellow-green). Style color: Closest to but brighter than RHS 137A (Green). Ovary arrangement: Parietal. Ovary interior color: RHS 145B (Yellow-green).

*Seed production*.—Not observed.

Disease and insect resistance: No particular resistance or susceptibility observed.

COMPARISON WITH PARENTAL LINES AND KNOWN VARIETY

'SAKIMP043' is distinguished from its parents as shown in Table 1.

TABLE 1

Comparison with Parental Lines

| Characteristic | 'SAKIMP043' | Female Parent 'NC-1H1' | Male Parent 'NJ-1174A' |
|---|---|---|---|
| Flower color | Blush-pink | Light-orange | Lavender |
| Plant growth habit | Spreading | Mounding | Mounding |

When 'SAKIMP043' is compared to the commercial *Impatiens* variety 'SAKIMP013' (U.S. Plant Pat. No. 19,597), the following differences as described in Table 2.

TABLE 2

Comparison with Similar Variety

| Characteristic | 'SAKIMP043' | 'SAKIMP013' |
|---|---|---|
| Growth habit | Spreading | Compact |
| Petal color, upper surface | Closest to but lighter than RHS 52C (Red) for most petals, other petals have a much lighter color closest to RHS 62D (Red-purple) | RHS 65C (Red-purple) |
| Petal color, lower surface | Closest to RHS 56A (Red) for most petals, but other petals have a much lighter petal color closest to but lighter than RHS 56C (Red) | RHS 65C (Red-purple) |
| Spur color | RHS 155C (White) with slight RHS 144C (Yellow-green) at the tip | RHS65D (Red-purple) |

We claim:

1. A new and distinct variety of New Guinea *Impatiens* plant named 'SAKIMP043' as described and illustrated herein.

* * * * *